United States Patent [19]

Segall et al.

[11] Patent Number: 5,138,110
[45] Date of Patent: Aug. 11, 1992

[54] PROCESS FOR THE PREPARATION OF ALKYL-HALIDES

[75] Inventors: Jeane Segall; Leonard M. Shorr, both of Haifa, Israel

[73] Assignee: Bromine Compounds Ltd., Beer-Sheva, Israel

[21] Appl. No.: 746,137

[22] Filed: Aug. 13, 1991

Related U.S. Application Data

[63] Continuation of Ser. No. 498,806, Mar. 23, 1990, abandoned.

[51] Int. Cl.$^5$ ............................................. C07C 17/16
[52] U.S. Cl. .................................................... 570/258
[58] Field of Search ........................................ 570/258

[56] References Cited

FOREIGN PATENT DOCUMENTS 1038150  8/1966  United Kingdom .

Primary Examiner—Howard T. Mars
Attorney, Agent, or Firm—Michael N. Meller

[57] ABSTRACT

A process for preparing lower alkyl-halides from the reaction of HX and the corresponding lower alcohol, wherein X represents a halogen atom, comprises continuously feeding HX and a lower alcohol to a reactor maintaining the instantaneous molar ratio of HX to the alcohol greater than 3, and continuously distilling off lower alkyl-halide and water from the reactor, continuously separating the lower alkyl-halide and water and recycling part of the said water to the distillation column to abate HX distillation from the reactor. High acid concentration and temperatures are maintained to obtain high yields and rapid conversion of alkanols.

13 Claims, 3 Drawing Sheets

PROCESS FOR THE PREPARATION OF ALKYL-HALIDES

This application is a continuation of application Ser. No. 498,806, filed Mar. 23, 1990, now abandoned.

FIELD OF THE INVENTION

The present invention relates to a process for preparing lower alkyl-halides, particularly alkyl bromides. More particularly, the invention relates to a continuous process by means of which lower alkyl-halides are prepared from HX and the corresponding lower alcohol in an aqeous solution of the acid.

BACKGROUND OF THE INVENTION

The reaction:

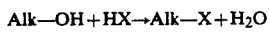

$$Alk{-}OH + HX \rightarrow Alk{-}X + H_2O$$

in which X represents a halogen atom, is generally known to take place. It is, however, considered to conform in type to the process of esterification, in which equilibrium between reactants and products is attained, as described by Migrdichian ["Organic Synthesis", Vol. 1, p.17, 1957, Reinhold Publishing Corp]. In practice, the preparation of alkyl halides in aqueous solution of the acid has been impractically slow, inefficient and in some cases even impossible to achieve. For this reason, even though aqueous HX is a very convenient form of HX and often the cheapest form available, the art has so far not provided an efficient process for the production of alkyl-halides in aqueous solutions of the acid, in good yield and with industrially acceptable rates. Thus Jolles ["Bromine and its Compounds", Ernest Benn Ltd., 1966, p.377] reports the preparation of 2-bromopentane in only 89% yield from the corresponding alcohol and 54% aqueous HBr in a 4 hour reaction in which two-thirds of the HBr must subsequently be discharged as waste. Norris [Am. Chem. J., 38, 627-42 (1907)] obtained similarly low yields of alkyl bromides by the slow distillation of product from mixtures of the corresponding alcohols in excess aqueous HBr, but under such conditions primary alcohols did not react with aqueous HCl.

In the case of such slow reactions with the lower alcohols, one cannot conceive to distil out the product alkyl halide and water as formed, and thus hope to maintain a constant acid concentration, because the alcohols themselves are very volatile and most of them form low boiling azeotropes with water and would thus be distilled out of the reactor before reacting. This is a serious limitation when operating with the process described by Norris. With methanol, the yield of $CH_3Br$ obtained by Norris was only 50%.

To promote such reactions it is common practice either to use anhydrous HX and operate in the vapor phase, or/and to employ dehydrating agents. Thus, sulfuric acid is commonly used for this purpose, sometimes both as a means of generating HX from a convenient salt (thus operating in an almost anhydrous mode) as well as to serve as a condensation agent. $ZnCl_2$ is commonly used in the case of $CH_3Cl$ manufacture in the liquid phase, and alumina often serves as catalyst for the manufacture of this material in the vapor phase [see, e.g., Weissermel and Arpe, "Industrial Organic Chemistry", Weinheim (1978), pp. 46-50].

It should be borne in mind that aqueous HX, on reacting in such processes, not only produces one mole of water for each mole of acid reacted, but at the same time liberates all of the water molecules which were associated with it in the original acid solution. Thus, on using 48% aqueous HBr, for each mole reacting 6 moles of water are liberated, which dilute the unreacted acid. The serious influence of the phenomena on reducing the reactivity of the remaining acid is immediately obvious.

In the cases of methyl bromide and methyl chloride, these can be produced by the halogenation of methane. This process is of industrial use in the case of methyl chloride if one has available a source of pure methane gas and can use the large amount of by-products (higher chlorinated methanes) coproduced [Weissermel and Arpe]. The corresponding reaction with bromine is not industrially useful.

Alkyl bromide can be produced by reacting the alcohol with elemental bromine and either phosphorus or sulfur. Elemental bromine is more expensive than HBr which is obtainable as a by-product in bromination reactions. Furthermore, the cost of using the phosphorus or the sulfur is increased even more, since these are converted into the corresponding acids in the reaction and become ecologically troublesome wastes. This reaction is nevertheless employed in the industrial manufacture of methyl bromide.

In spite of the failure of previous attempts to obtain high yields and rapid conversions of alkanols to alkyl halides in aqueous HX, it has now been found that it is possible to obtain the desired result if both the acid concentration and the temperature are high enough, and the instantaneous molar ratio of HX to alkanol is greater than 3. This is accomplished by continuously feeding HX and a lower alcohol to a reactor containing aqueous HX maintained under the appropriate conditions and lower alkyl-bromide and water are continuously distilled off from the said reactor, the lower alkyl-bromide and water being continuously separated, and part of the said water being recycled to the distillation column to abate HBr distillation from the reactor.

SUMMARY OF THE INVENTION

It has thus been found, and this is an object of the invention, that it is possible to provide a continuous process which is both simple and economic, and which permits to prepare alkyl halides in good yield and high purity.

It is another object of the invention to provide a process which can employ HBr in different forms, whether gaseous or aqueous. Even HBr from waste streams which contain organic contaminants whose boiling point, or those of their azeotropes, are below that of 48% aqueous HBr is useful in the process of this application. This fact, as will be apparent to the skilled engineer, renders the process of the invention an attractive way to employ HBr obtained as by-product in various processes. For instance, in UK Patent Application GB 2,219,583 of the same applicant, there is disclosed a process for the bromination of $CH_3Br$ to dibromomethane (DBM), which produces HBr as a useful by-product, which HBr can be conveniently employed in the process of the invention.

In order for the process to be convenient and effective, it is desirable to operate in such a way that reaction rates are high, and the concentration of HX in the distillate water is low. It was been found that this can be achieved, when employing the process of the invention, by operating close to the azeotropic composition of HX/water mixtures, viz., close to 48% for HBr and 20% for HCl. Thus it is preferred to operate at an HBr concentration of about 42–46%, and an HCl concentration of about 19%. Since in the process water is formed, relatively large amounts of water distill off, and the HX/water composition may be maintained substantially constant by keeping the temperature of the reaction mixture at about 120°–123° C. for HBr and 108°–109° C. for HCl. As will be apparent to the skilled engineer, the boiling point of the reaction mixture may be lowered by the presence of impurities. In the case that contaminants are present, the term "azeotropic composition" must be interpreted so as to take into account the effect of such impurities on the boiling point of the mixture, rather than as referring to that of pure components. The temperatures mentioned above, therefore, may vary according to the specific case.

BRIEF DESCRIPTION OF THE DRAWINGS

The above and other characteristics and advantages of the invention will be better understood from the following illustrative and non-limitative examples, and with reference to the appended drawings wherein.

Figure 1:
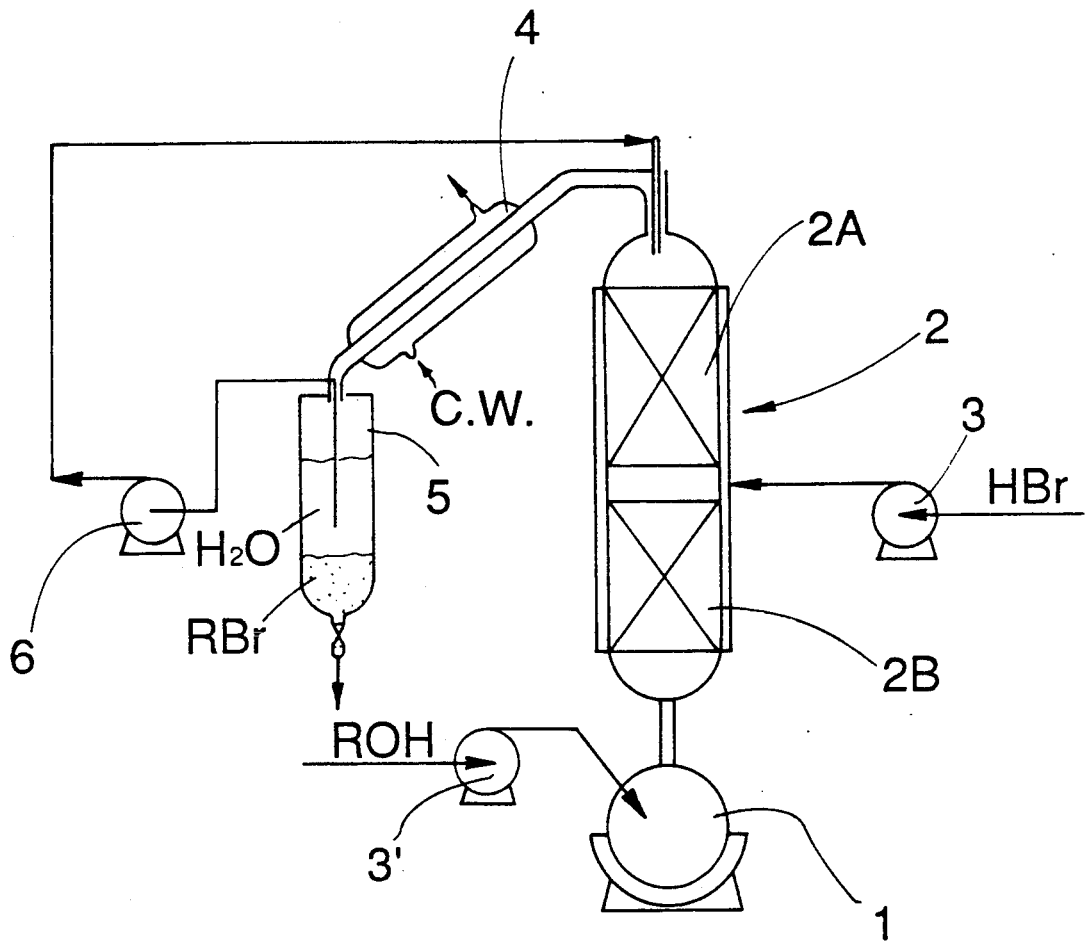
FIG. 1 is a schematic representation of a bench experimental system.

With reference now to FIG. 1, the laboratory system comprises a 0.5 liter reactor, indicated by numeral 1, which is electrically heated. A packed column 2, mounted above the reactor, has a diameter of 5 cm and contains 10 mm Raschig rings, with a packing height of 60 cm. The column is divided into two sections (2A and 2B), and HBr is fed at the center of the column (height: 30 cm), through a metering pump 3. The alcohol is fed to the reactor via a metering pump 3'.

A condenser 4 is mounted above the column 3, to condense alkyl bromide and water which are separated in a phase-separator 5. Water from the separator 5 is refluxed via a recycle metering pump 6 to the head of the column 2. Temperature control is achieved by controlling the amount of heat supplied to the reactor.

Figure 2:
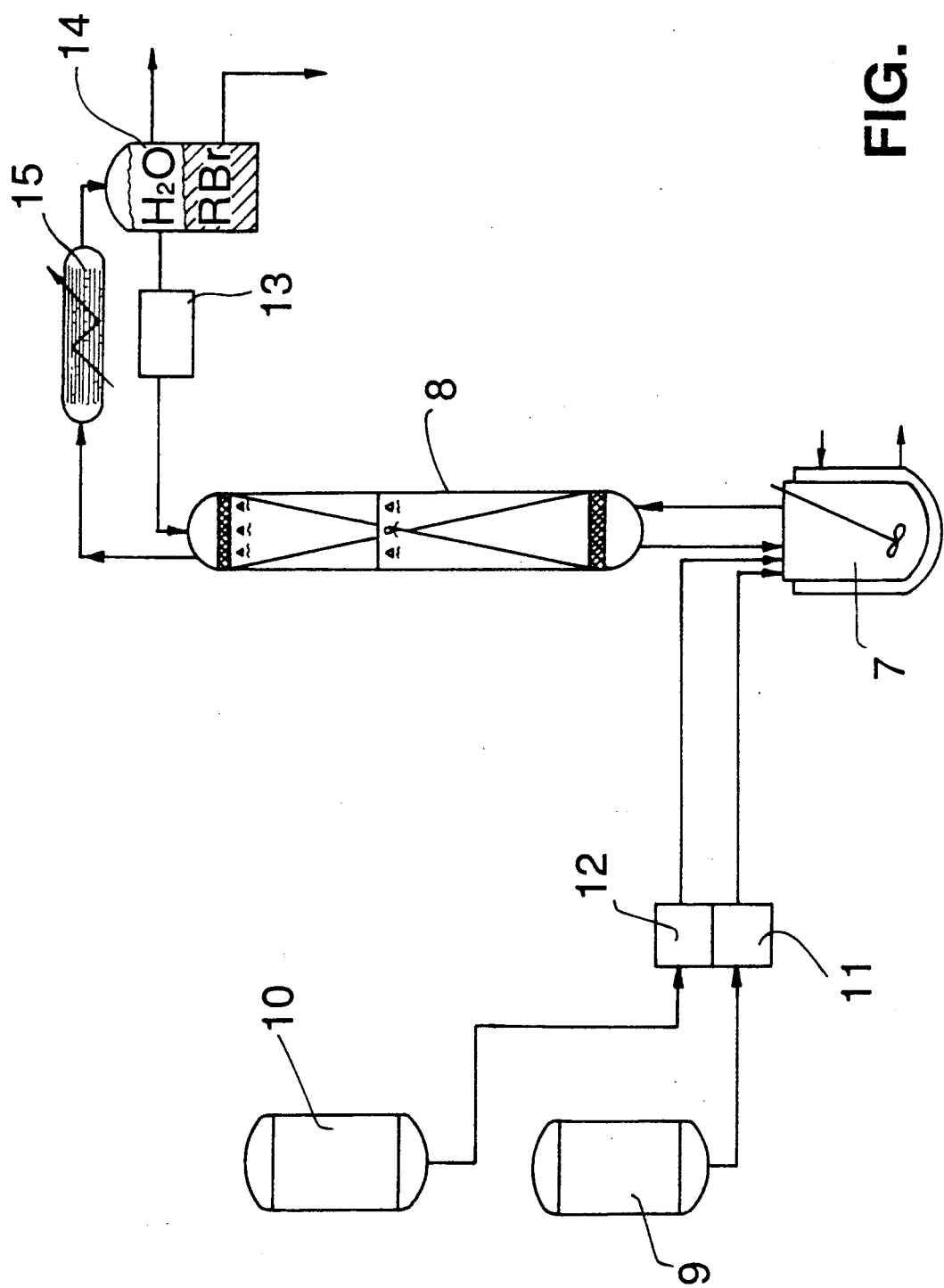
FIG. 2 is a pilot plant constructed according to one embodiment of the invention.

FIG. 2 shows the pilot plant in which several experimental runs detailed below were carried out. In this plant the reactor 7 is a 100 liter glass-lined reactor, equipped with a steam jacket, an agitator and standard accessories. The bubble-caps distillation column 8 has a diameter of 4" and contains 12 actual plates made of Teflon and separated from one another by a space of 6". The area of the cap holes of each plate is 8.2 cm². An alcohol supply tank 9 and an aqueous HBr supply tank 10 are provided, as well as respective metering pumps 11 and 12. An additional metering pump 13 is provided for recycling water which separates in the $H_2O$/AlkBr phase-separator 14, after condensing in the condenser 15. Surplus separated water is disposed of as waste product.

Figure 3:
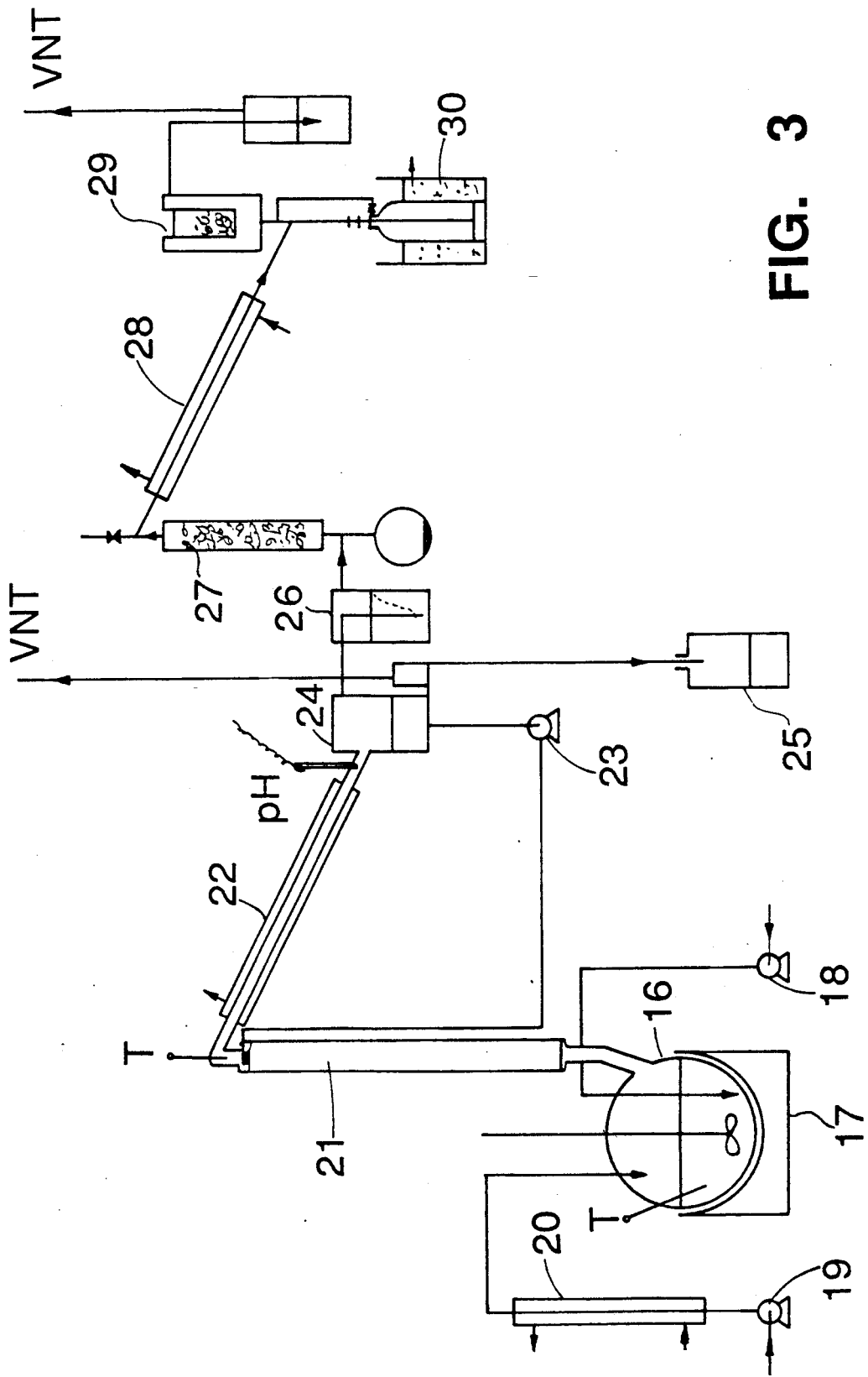
FIG. 3 is an alternative experimental system.

In FIG. 3 the pot 16 is heated by an electric heater, and comprises a mechanical stirrer and other standard fittings, such as a thermometer. Alcohol is fed by a pump 18, and the acid by pump 19 and through a preheater 20. The distillation column 21 is fitted with a condenser 22 and receives a reflux stream via a reflux pump 23. A phase-separator 24, a waste water reservoir 25 and an acid neutralization tank 26, containing 15% NaOH solution, are connected downstream. The drying and storage step comprises a column 27, filled with $CaCl_2$, to which the alkyl halide leaving the neutralization tank 26 is fed, a heat-exchanger 28, an acetone/-$CO_2$ trap 29 and an alkyl halide storage tank 30, cooled by ice.

The operation of the bench and pilot experimental systems is self-evident to the skilled engineer, from the description given above, and will be further illustrated by the following examples.

EXAMPLE 1

Several experimental runs were carried out to determine the influence of the molar ratio HBr (aq)/MeOH. The experiments were carried out with MeOH (Fluka) and 48% HBr (Merck). Reactions were carried out with 2 ml samples placed in 10 ml flasks fitted with a condenser and a thermometer. The samples were heated to the reaction temperature during less than 1 minute, by placing them in a thermostated bath preheated to about 140° C. After the predetermined reaction time lapsed, the reaction was virtually stopped by rapidly inserting the flask into an ice-cold bath. The total acidity (HBr) left in the sample was analyzed. The difference in HBr concentration corresponds to the amount of MeBr formed. The results of these experiments are set forth in Table I, from which it can be seen that by increasing the molar ratio of HBr/MeOH from 3 to 10, the time of complete reaction is shortened from 30 to 3 minutes.

EXAMPLE 2

Kinetic experiments were carried out, similarly to those described in Example 1, but varying the initial HBr concentration (in the range 42–48 wt %), at an initial fixed HBr/MeOH molar ratio (2/1). The results are summarized in Table II. Lowering the initial HBr concentration from 48% to 42% sensibly increases the reaction time.

EXAMPLE 3

Several experimental runs were carried out in the laboratory unit of FIG. 1, by feeding ethanol to the reactor at rates of 0.9–1.8 mol/lit.-hr. The 48% HBr was fed continuously to the center of the column at an equivalent molar rate. The concentration of HBr in the reactor was maintained constant at 44.5%–46.5% by controlling the temperature of the liquid at 120°–123° C. The product and water were collected continuously from the distillate. Part of the water was recycled at a reflux ratio of 0.5–1.5, to remove HBr from the distillate and to maintain the neutrality of the effluent water. The best and worst product compositions obtained are shown in Table III, from which it can be seen that excellent results are obtained throughout the range of parameters described. The distillate water collected contained 1–1.7% EtBr and 0,3–0,5 EtOH. The yield based on alcohol was 90–95%.

EXAMPLE 4

Example 3 was repeated, but employing i-Propanol instead of ethanol. The feed rate was 1.2–1.7 mol/lit.-hr. The reactor temperature was 122°–124° C. and the HBr concentration in the reactor was 46–47%. The reflux ratio varied between 0.5–1.0. The results are shown in Table IV, and are similar to those obtained in Example 3. The distillate water contained about 1.1% i-PrOH and about 0.3% i-PrBr. The maximal HBr concentration in the water was 0.12%. The actual yield based an alcohol was >95%.

EXAMPLE 5

Example 3 was repeated, but employing n-Butanol as the alcohol. The feed rates employed were 0.65-2.1 mol/lit.-hr, the reactor temperature was 120°-123° C., and the water reflux ratio 0.4-1.2.

The results of those experiments are summarized in Table V. It should be noted that increasing the HBr concentration from about 44 to 46.5% lowers the amount of unreacted alcohol by one order of magnitude.

EXAMPLE 6

Example 5 was repeated, but n-BuOH was fed as a vapor. For this purpose, an evaporator was introduced in line after the alcohol metering pump (3' in FIG. 1). By this means, better thermal control was achieved than in Example 5, and less fluctuations in the reactor temperature resulted. This led to better control of the reaction as well as better average results. The experimental results detailed in Table VI show an improvement in the process rate, as compared to the results of Example 5, as well as a drop in the extent of i-BuBr formation. The distillate water at a reflux ratio of 1 was neutral.

EXAMPLE 7

Reaction of HBr and i-PrOH was carried out in the pilot plant of FIG. 2. The reaction temperature was 121°-124° C., the feed rate 50-70 mol/hr, and the reflux ratio was 1-1.5. The HBr (48%) was preheated to 110° C. and fed to the center of the column 8 of FIG. 2. Typical results are shown in Table VII.

EXAMPLE 8

Example 7 was repeated, using n-BuOH as the alcohol. The temperature employed was 120°-123° C., the feed rate 40-65 mol/hr and the reflux ratio was 1.1-1.5. Different runs were carried out feeding the HBr either to the center of the column or directly to the reactor. This change did not affect the quality of the product obtained. Also increasing the stirring speed form 50 to 110 rpm did not increase the process rate significantly. Typical results for this run are shown in Table VIII.

Table IX shows a typical distribution of materials in the distillation column, from which it can be seen that essentially all the reaction takes place within the reactor.

EXAMPLE 9

Example 8 was repeated, feeding HBr directly to the reactor and using n-PrOH as the alcohol, with a feed rate of 60-90 mol/hr. The results are shown in Table X.

EXAMPLE 10

Example 9 was repeated, using EtOH, with a feed rate of 90-100 mol/hr and a reflux ratio of 0.8-1.2. The results are shown in Table XI.

EXAMPLE 11

Experiments with n-BuOH were performed using a column packed with Raschig rings, and feeding HBr directly to the reactor via a dip pipe. The feed rate was 50-75 mol/hr and the reflux ratio was 0.8-1.5. The reactor temperature was maintained at 121°-123° C. The packed column consisted of two sections: the lower, of packing height 87 cm, and the upper of packing height 61 cm. The results obtained are shown in Table XII.

EXAMPLE 12

Example 11 was repeated, but using a 62% aqueous HBr solution. The reflux ratio was in this case 1.2-1.7. The results obtained were as in Example 11.

EXAMPLE 13

Experiments were carried out in the set-up of FIG. 3, by feeding to the reactor containing aqueous HBr, equimolar amounts of methanol and aqueous 48% HBr, and maintaining in the reactor, at about 118°-121° C., a constant HBr concentration (~44-46%), by continuous removal of the water by distillation.

The results, summarized in Table XIII, show that at an hourly reagents feed rate of 1.6-4.1 mole/lit. reactor, 0.15-0.4 Kg/lit. reactor of 99-99.9% pure methyl bromide are formed.

EXAMPLE 14

Example 13 was repeated by feeding to the reactor containing aqueous HBr, equimolar amounts of methanol and aqueous 48% HBr, which also contained 0.5% dibromomethane (DBM) as an impurity. At an hourly reagents feed rate of about 3 mole/lit. reactor and 119° C. in the pot, 290 g/lit. reactor of 99.8% pure methyl bromide were produced. The DBM present in the aqueous HBr feed was removed from the bottom of the aqueous distillate.

EXAMPLE 15

Example 14 was repeated under identical conditions, using as feed aqueous HBr contaminated with 1% acetic acid. Methyl bromide 99.8% pure was produced. Acetic acid and some methyl acetate were found in the aqueous distillate.

EXAMPLE 16

The set-up of FIG. 3 was used, employing a 45×2 cm distillation column filled with 0.3 cm Wilson glass helices. Aqueous 20% HCl was placed in the reactor which was heated and maintained at 110° C. Equimolar quantities of methanol and aqueous 20% HCl were fed to the reactor at a rate of about 0.3 mole/lit. reactor, while the aqueous distillate was removed continuously. The methyl chloride which formed, flashed out of the reaction zone, was condensed and found to be 99% pure.

EXAMPLE 17

Example 16 was repeated, using instead of methanol n-propanol. By continuous water removal in the distillate, the reaction proceeded to produce n-propyl chloride, 98% pure.

EXAMPLE 18

Example 13 was repeated, using anhydrous HBr gas instead of aqueous HBr. The initial acid concentration in the reactor was 45-6% and it was kept in this strength by maintaining a temperature of 121° C. The reagent feed was equimolar throughout, and the feed rate was 2.6 mole/l reactor.

Methyl bromide of 99.5% purity was obtained along with distillate water containing only 0.3% HBr. The volume of the aqueous distillate was only 17% of that produced when using 48% HBr. The thermal requirements for distillation were therefore considerably reduced.

The above description and examples have been provided for the purpose of illustration, and are not intended to be limitative. Many variations can be effected in the process of the invention. Different ways can be exploited for feeding HX to the reactor, at different feed points and in different concentrations, or different temperatures and reflux ratios can be used, all without exceeding the scope of the invention.

TABLE I

Rate of MeBr Formation at Various Molar Ratios of HBr[a]/MeOH

| HBr/MeOH mole/mole | Time mins. | Temperature °C. | MeBr Formation % mole |
|---|---|---|---|
| 1/1 | 10 | 106 | 42 |
|  | 20 | 109 | 54 |
|  | 40 | 110 | 59 |
|  | 90 | 110 | 63 |
| 3/1 | 3 | 116 | 67 |
|  | 4 | 117 | 71 |
|  | 5 | 117 | 73 |
|  | 8 | 120 | 76 |
|  | 10 | 120 | 82 |
|  | 20 | 120 | 92 |
|  | 30 | 120 | 99 |
| 10/1 | 2 | 108 | 76 |
|  | 3 | 118 | 99 |

[a]HBr 48% w/w used throughout

TABLE II

Rate of MeBr Formation at Various Initial HBr Concentrations

| Initial HBr Conc. % w/w | Time mins. | Temperature °C. | MeBr Formation % mole |
|---|---|---|---|
| 42 | 5 | 111 | 39 |
|  | 20 | 111 | 66 |
|  | 40 | 111 | 76 |
|  | 90 | 111 | 86 |
| 45 | 5 | 112 | 53 |
|  | 40 | 112 | 85 |
|  | 90 | 114 | 84 |
| 48 | 5 | 112 | 62 |
|  | 10 | 113 | 79 |
|  | 15 | 113 | 87 |
|  | 30 | 113 | 89 |

TABLE III

Experimental Results with Ethanol

|  | Ethyl Bromide (%) | ethyl ether (%) | Ethanol (%) |
|---|---|---|---|
| Best: | 99.9 | 0.074 | 0.049 |
| Worst: | 99.6 | 0.140 | 0.080 |

TABLE IV

Experimental Results with i-Propanol

|  | i-Propyl Bromide (%) | i-Propanol (%) | Propylene (%) |
|---|---|---|---|
| Best: | 99.6 | 0.26 | 0.13 |
| Worst: | 99.2 | 0.51 | 0.25 |

TABLE V

Experimental Results with n-Butanol

| i-BuBr (%) | n-BuOH (%) | n-BuBr (%) | HBr Conc. in Reactor (%) | Reaction Rate [mol/lit-hr] |
|---|---|---|---|---|
| 0.95 | 13.4 | 85.6 | 43.6 | 1.98 |
| 0.84 | 12.5 | 86.5 | 43 | 1.12 |
| 1.2 | 2.83 | 95.6 | 44.2 | 1.12 |
| 1.2 | 1.3 | 97.4 | 46.5 | 1.06 |
| 1.2 | 3.0 | 95.5 | 47 | 2.1 |
| 1.2 | 1.3 | 97.2 | 46.8 | 0.98 |

TABLE VI

Experimental Results with n-Butanol Fed As A Vapor

| i-BuBr (%) | n-BuOH (%) | n-BuBr (%) | HBr Conc. in Reactor (%) | Reaction Rate [mol/lit-hr] |
|---|---|---|---|---|
| 0.77 | 0.47 | 98.63 | 46.5 | 0.96 |
| 0.78 | 1.40 | 97.75 | 46.6 | 1.65 |

TABLE VII

Pilot Results with i-PrOH

|  | i-PrBr (%) | i-PrOH (%) | Propylene (%) |
|---|---|---|---|
| Best: | 99.6 | 0.06 | 0.12 |
| Normal: | 98.6 | 0.24 | 0.25 |
| Worst: | 95.9 | 3.24 | 0.60 |

TABLE VIII

Pilot Results with n-BuOH

|  | Alcohol in Water | Product Composition | | |
|---|---|---|---|---|
|  | n-BuOH (%) | n-BuOH (%) | i-BuBr (%) | n-BuBr (%) |
| Best: | 0.7 | 0.6 | 1.10 | 98.2 |
| Normal: | 1.1 | 1.1 | 0.90 | 98.0 |
| Worst: | 2.0 | 2.0 | 0.87 | 97.0 |

TABLE IX

Vapor Composition in Column

| Plate No. | Phase | Product Composition | | | |
|---|---|---|---|---|---|
|  |  | n-BuOH (%) | i-BuBr (%) | n-BuBr (%) | HBr (%) |
| 1 | Organic | 0.35 | 1.1 | 98 | — |
| 5 | " | 0.57 | 1.1 | 98 | — |
| 1 | Aqueous | 0.71 | — | — | 30.6 |
| 5 | " | 0.71 | — | — | 12.8 |

TABLE X

Pilot Results with n-PrOH

|  | Alcohol in Water | Product Composition | | |
|---|---|---|---|---|
|  | n-PrOH (%) | n-PrOH (%) | i-PrOH (%) | n-PrBr (%) |
| Best: | 0.65 | 0.20 | 0.61 | 98.7 |
| Normal: | 2.10 | 0.50 | 0.98 | 98.4 |
| Worst: | 3.50 | 0.76 | 1.10 | 98.2 |

TABLE XI

Pilot Results with Ethanol

|  | Organic in Distillate Water | Product Composition | | | |
|---|---|---|---|---|---|
|  | EtOH (%) | EtBr (%) | Et$_2$O (%) | EtOH (%) | EtBr (%) |
| Best: | 0.25 | 0.26 | 0.01 | 0.03 | 99.9 |
| Normal: | 0.50 | 0.90 | 0.03 | 0.04 | 99.9 |
| Worst: | 0.73 | 0.90 | 0.04 | 0.07 | 99.8 |

TABLE XII

Pilot Results with n-BuOH

|  | Distillate Water | Product Composition | | |
|---|---|---|---|---|
|  | n-BuOH (%) | n-BuOH (%) | i-BuBr (%) | n-BuBr (%) |
| Best: | 1.3 | 1.05 | 0.58 | 98.1 |
| Normal: | 1.7 | 1.50 | 0.70 | 97.7 |

TABLE XIII

Methyl Bromide Synthesis in a Continuous Reactor

| Run No. | CH$_3$OH Mole Lit React. | Temperature °C. Pot | Temperature °C. Head | CH$_3$Br Formed g Lit React. | CH$_3$Br Formed % Purity | Aq. Distillate HBr % | Aq. Distillate CH$_3$OH % | Aq. Distillate CH$_3$Br % |
|---|---|---|---|---|---|---|---|---|
| 1 | 1.6 | 121 | 89 | 152 | 99.9 | 0.3 | 0.2 | 0.1 |
| 2 | 2.7 | 120 | 88 | 256 | 99.7 | 0.4 | 0.4 | 0.3 |
| 3 | 4.1 | 118 | 87 | 390 | 99.1 | 0.2 | 0.8 | 0.3 |

We claim:

1. A process for preparing lower alkyl bromides from the reaction of HBr and the corresponding lower alcohol, wherein HBr and a lower alcohol are continuously fed to a reactor containing aqueous HBr and lower alkyl bromide and water are continuously distilled off from the said reactor through a distillation column, the lower alkyl bromide and water being continuously separated and part of the said water being recycled to the distillation column to abate HBr distillation from the reactor, the instantaneous molar ratio of HBr to the alcohol being greater than 3, the concentration of HBr in the reactor being about 43-46% by weight and the temperature of the reaction mixture being about 120°-123° C.

2. A process according to claim 1, wherein the concentration of HBr in the reactor is maintained substantially constant by adjusting the temperature of the reaction mixture.

3. A process according to claim 1, wherein the alcohol is fed in liquid form.

4. A process according to claim 1, wherein the alcohol is fed in vapor form.

5. A process according to claim 1, wherein HBr is fed in gaseous form.

6. A process according to claim 1, wherein HBr is fed in liquid form.

7. A process according to claim 6, wherein the liquid form is about a 48% aqueous solution of HBr.

8. A process according to claim 6, wherein the liquid form is about a 62% aqueous solution of HBr.

9. A process according to claim 1, wherein HBr contains impurities having a boiling point below that of a 48% aqueous solution of HBr, or which form aqueous azeotropes having a boiling point below that of a 48% aqueous solution of HBr.

10. A process according to claim 9, wherein the impurities comprise dibromomethane and/or CH$_3$COOH.

11. A process according to claim 1, wherein the HBr employed is the product of the bromination reaction of CH$_3$Br to dibromomethane.

12. A process according to claim 1, wherein the lower alcohol is a C$_1$-C$_4$ alcohol.

13. A process according to claim 12, wherein the alcohol is selected from the group consisting essentially of MeOH, EtOH, i-PrOH, n-PrOH and n-BuOH.

* * * * *